US010278637B2

(12) United States Patent
Sheinkopf et al.

(10) Patent No.: US 10,278,637 B2
(45) Date of Patent: May 7, 2019

(54) ACCURATE ANALYSIS TOOL AND METHOD FOR THE QUANTITATIVE ACOUSTIC ASSESSMENT OF INFANT CRY

(71) Applicants: BROWN UNIVERSITY, Providence, RI (US); WOMEN & INFANTS HOSPITAL OF RHODE ISLAND, Providence, RI (US)

(72) Inventors: Stephen J. Sheinkopf, Barrington, RI (US); Barry M. Lester, Warwick, RI (US); Harvey F. Silverman, East Greenwich, RI (US)

(73) Assignees: Brown University, Providence, RI (US); Women & Infants Hospital of Rhode Island, Providence, RI (US)

( * ) Notice: Subject to any disclaimer, the term of this patent is extended or adjusted under 35 U.S.C. 154(b) by 813 days.

(21) Appl. No.: 14/633,224

(22) Filed: Feb. 27, 2015

(65) Prior Publication Data

US 2015/0265206 A1 Sep. 24, 2015

Related U.S. Application Data

(63) Continuation of application No. PCT/US2013/057295, filed on Aug. 29, 2013.
(Continued)

(51) Int. Cl.
| | | |
|---|---|---|
| A61B 5/00 | (2006.01) | |
| A61B 5/16 | (2006.01) | |
| A61B 5/12 | (2006.01) | |
| G10L 25/90 | (2013.01) | |
| G10L 25/78 | (2013.01) | |
| G10L 17/26 | (2013.01) | |
| G10L 25/66 | (2013.01) | |
| G10L 25/18 | (2013.01) | |

(52) U.S. Cl.
CPC ............ *A61B 5/4803* (2013.01); *A61B 5/121* (2013.01); *A61B 5/16* (2013.01); *A61B 5/4076* (2013.01); *G10L 17/26* (2013.01); *G10L 25/18* (2013.01); *G10L 25/66* (2013.01); *G10L 25/78* (2013.01); *G10L 25/90* (2013.01); *A61B 5/7257* (2013.01); *A61B 5/7275* (2013.01); *G10L 2025/906* (2013.01)

(58) Field of Classification Search
CPC ............................ A61B 5/4354; A61B 5/4803
See application file for complete search history.

(56) References Cited

U.S. PATENT DOCUMENTS

| | | | |
|---|---|---|---|
| 2,691,137 A | 10/1954 | Smith | |
| 2008/0235030 A1* | 9/2008 | Sisto | ........................ G10L 17/26 704/275 |
| 2014/0122063 A1* | 5/2014 | Gomez Vilda | .......... G10L 19/02 704/200.1 |

OTHER PUBLICATIONS

Fort, Ada, and Claudia Manfredi. "Acoustic analysis of newborn infant cry signals." Medical engineering & physics 20.6 (1998): 432-442.*

(Continued)

*Primary Examiner* — Sean P Dougherty
*Assistant Examiner* — Nicholas E Kolderman
(74) *Attorney, Agent, or Firm* — Preeti T. Arun; Sonia K. Guterman; Lawson & Weitzen LLP

(57) ABSTRACT

An automated infant cry analyzer with high accuracy to detect important acoustic features of cry is provided. The system's accuracy was rigorously tested and was compared to ground truth manual coding. The resulting methods and systems are applied to infant developmental disorders.

23 Claims, 7 Drawing Sheets

Related U.S. Application Data

(60) Provisional application No. 61/718,384, filed on Oct. 25, 2012, provisional application No. 61/694,437, filed on Aug. 29, 2012.

(56) References Cited

OTHER PUBLICATIONS

Manfredi, C., et al. "High-resolution cry analysis in preterm newborn infants." Medical engineering & physics 31.5 (2009): 528-532.*
Goberman, Alexander M., and Michael P. Robb. "Acoustic examination of preterm and full-term infant cries: The long-time average spectrum." Journal of Speech, Language, and Hearing Research 42.4 (1999): 850-861.*
Branco et al. (2007) The newborn pain cry: Descriptive acoustic spectrographic analysis. International Journal of Pediatric Otorhinolaryngology, 71, 539-546. doi: 10.1016/j.ijporl.2006.11.009.
Dubnowski et al. (1976) Real-time digital hardware pitch detector. IEEE Trans on ASSP, 24, 2-8.
Goberman et al. (1999) Acoustic examination of preterm and full-term infant cries: the long-time average spectrum. Journal of Speech Language and Hearing Research, 42, 850-61.
Lagasse et al. (2005) Assessment of infant cry: acoustic cry analysis and parental perception. Mental Retardation and Developmental Disabilities Research Reviews, 11, 83-93. doi: 10.1002/mrdd.20050.
Lester et al. (1991) Neurobehavioral syndromes in cocaine-exposed newborn infants. Child Development, 62, 694-705.
Lester et al. (2002) The maternal lifestyle study: effects of substance exposure during pregnancy on neurodevelopmental outcome in 1-month-old infants. Pediatrics, 110, 1182-1192. doi: 10.1542/peds.110.6.1182.
Mampe et al. (2009) Newborns' cry melody is shaped by their native language. Current Biology, 19, 1994-1997. doi:10.1016/j.cub.2009.09.064.
Manfredi et al. (2009) High-resolution cry analysis in preterm newborn infants. Medical Engineering & Physics, 31, 528-532. doi: 10.1016/j.medengphy.2008.10.003.
Martin (1981) Extraction de la frequence fondamentale par intercorrelation avec une function peigne. Journees d Etude sur la Parole, 12, 221-232.
Noll (1967) Cepstrum pitch determination. Journal of the Acoustical Society of America, 40, 1241.
Rabiner (1977) On the use of autocorrelation analysis for pitch detection. IEEE Trans on ASSP, 25, 24-33.
Rader (1964) Vector pitch detection. Journal of the Acoustical Society of America, 36, 1463.
Robb et al. (1995) Estimation of formant frequencies in infant cry. International Journal of Pediatric Otorhinolaryngology, 32, 57-67. doi:10.1016/0165-5876(94)01112-b.
Secrest et al. (1982) Postprocessing techniques for voice pitch trackers. In Proc. icassp '82. (vol. 7, p. 172-175).
Varallyay (2004) Acoustic analysis of the infant cry: classical and new methods. Conf Proc IEEE Eng Med Biol Soc, 1, 313-316.
Wermke et al. (2007) Relation of melody complexity in infants' cries to language outcome in the second year of life: a longitudinal study. Clinical Linguistics and Phonetics, 21, 961-973. doi:10.1080/02699200701659243.
Wermke et al. (2002) Developmental aspects of infant's cry melody and formants. Medical Engineering and Physics, 24(7-8), 501-514. doi:S1350453302000619.
International Search Report and Written Opinion of the International Searching Authority for PCT/US13/57295 dated Dec. 26, 2013 (11 pgs.).

* cited by examiner

ACCURATE ANALYSIS TOOL AND METHOD FOR THE QUANTITATIVE ACOUSTIC ASSESSMENT OF INFANT CRY

RELATED APPLICATIONS

The present application is a continuation of and claims the benefit of international application serial number PCT/US2013/057295 filed Aug. 29, 2013, which claims the benefit of U.S. provisional application Ser. No. 61/694,437 filed Aug. 29, 2012, and Ser. No. 61/718,384 filed Oct. 25, 2012 entitled, "Accurate analysis tool and method for the quantitative acoustic assessment of infant cry" by Stephen J. Sheinkopf, Barry M. Lester and Harvey F. Silverman, each of which is hereby incorporated herein by reference in its entirety.

GOVERNMENT SUPPORT

The invention was made with government support under grant number R21 DC010925 awarded by the National Institutes of Health. The government has certain rights in the invention.

TECHNICAL FIELD

Apparatus and methods are provided for quantitative acoustic accurate assessment of infant cry.

BACKGROUND

Infants are afflicted with various developmental disorders for example autism spectrum disorders, Asperger's syndrome, Down's syndrome, cerebral palsy, velocariofacial syndrome, Klinefelter's syndrome, William's syndrome, Prader-Willi syndrome, Mowat-Wilson syndrome, and neurofibromatosis. Neurodevelopmental disorders in infants impair growth and development of brain or central nervous system producing neurodevelopmental consequences. Early intervention is one of the most promising treatments for developmental disorders but requires early diagnosis to be most effective.

Acoustic analysis of infant cry has been a focus of clinical and developmental research for a number of years. Although a variety of approaches to cry analysis have been employed, each has its drawbacks. Applied and clinical studies of infant cry have examined features of cry production that may distinguish babies with specific conditions or medical risks. Lester et al., utilizes infant cry analysis as a measure of developmental status in babies with pre- and peri-natal risk factors, such as prenatal substance exposure. Lester et al., *Pediatrics*, 110, 1182-1192 (2002). Goberman & Robb, 1999 analyzes infant cry for premature birth. Goberman, A. M, and Robb, M. P. *Journal of Speech, Language and Hearing Research*, 42, 850-861 (1999). Sheinkopf et al., analyzes infant cry for autism. Sheinkopf et. al., *Autism Research*, 5, 331-339 (2012).

In response to a pain stimulus, the cry acoustics for an infant at risk for autism is atypical and high-pitched. Ibid., p 6 ¶ 2.

Manual inspection of spectrograms is the standard method for detecting acoustic features in cry sounds, including the timing and onset of cry vocalizations and, the fundamental frequency of cry. However, the manual inspection method is slow, limiting the amount of data that can be analyzed and requires trained observers to visually inspect the spectrograms. There is a need for a non-invasive, fast, automatic and accurate test for diagnosing infant developmental disorders, yielding early detection and a capability of early intervention in treatment of the developmental disorders.

SUMMARY

The invention provides a method and an apparatus for analysis of infant cry to robustly and accurately identify features thereof. Identified features may form a record printout, and atypical features can be correlated with a diagnosis made by conventional means at a later time (e.g., in childhood, post-verbal) to develop a measure or table of diagnostic indicia, and/or features may be compared to a known list or table of known or suspected condition-indicating atypical features associated with specific medical, developmental, disease or injury conditions. The method and apparatus may be automated for easy application to an infant, and may be applied to selected at-risk infants for earlier detection and, where appropriate, intervention. It may also be applied to confirm or refine a diagnosis, or to follow progression of a condition. Advantageously, the apparatus may be set up to receive, make or operate upon a digital recording in an industry standard format, such as a 48,000 sample-per-second (48 ks/s) 16-bit recording format of a consumer device, and to quickly and automatically derive the resultant features and measures. When used as a standardized clinical instrument providing a defined stimulus and controlled recording, the processed records offer greater sensitivity, accuracy and the ability to identify diagnostic features present in short sound records and to identify new anomalies or indicia not otherwise apparent even to an experienced clinician or technician.

An aspect of the invention herein provides a method for analyzing infant cry, the method including
  filtering a digital recording of an infant cry, by assigning to a digital signal of the recording: a fixed frame rate of a plurality of samples, a window function, and a frame advance, thereby obtaining an altered digital signal, and limiting a range of accepted frequency by applying a frequency window to a log-spectrum of the altered digital signal, such that the frequency window is from about 200 Hz to about 2200 Hz, and in this way obtaining a first filtered digital signal, so that the first filtered digital signal is a frequency window output;
  estimating a fundamental frequency ($F_0$) and a cepstrum value of the infant cry by applying to the first filtered digital signal an inverse Discrete Fourier Transform to obtain the fundamental frequency and cepstrum estimate value of the first filtered digital signal, and in this way obtaining a second filtered digital signal;
  smoothing the second filtered digital signal by applying a programming smoother to the second filtered digital signal and maintaining continuity in the fundamental frequency estimates of the second filtered digital signal, eliminating outliers from the second filtered digital signal by applying a median filter, such that the median filter is selected from a group of a median filters of five point and seven point median filters, to the second filtered digital signal and obtaining a median output, extracting a confidence measure from at least one of the first filtered digital signal values and the second filtered digital signal on a frame by frame basis, and applying to the median output a signal-to-noise ratio test, and in this way obtaining at least one parameter of acoustic analysis of the infant cry.

An embodiment of the method further includes estimating the fundamental frequency of the first filtered digital signal, if greater than about 800 Hz, by applying an interpolated transform of 4096 points and a low pass filter.

An embodiment of the method further includes, after applying the signal to noise ratio test, classifying a sound segment of the infant cry within the parameters as at least one of: an utterance, a short utterance, and a silence, such that the sound segment comprises a group of frames having similar properties.

An embodiment of the method further includes characterizing a sound segment record by each of elements: classifier output, timing parameters, $F_0$ parameters, hyper-pitch parameters, formant parameters, parameters from fitting a polynomial to the pitch contour, and parameters for amplitudes from several octave frequency bands.

In an embodiment of the method the parameter of acoustic analysis includes at least one of: frame number, time (ms), $F_0$, $F_0$ amplitude (dB), $F_0$ confidence [0-1], Hyper-pitch (Hz) ([1-5] kHz range), Hyper-pitch amplitude (dB), Hyper-pitch confidence [0-1], Peak pitch amplitude (dB), Overall amplitude (dB), Amplitude [0.5-10] kHz (dB), Amplitude [0-0.5] kHz (dB), Amplitude [0.5-1] kHz (dB), Amplitude [1-2.5] kHz (dB), Amplitude [2.5-5] kHz (dB), Amplitude [5-10] kHz (dB), $F_1$ (Hz), Amplitude of $F_1$ (dB), $F_2$ (Hz), Amplitude of $F_2$ (dB), $F_3$ (Hz), and amplitude of $F_3$ (dB).

An embodiment of the method further includes, prior to filtering the digital recording, converting the digital recording into a computer readable format by a computer program embedded in a non-transitory computer readable medium.

In an embodiment of the method, the utterance has a signal length equal to or greater than 0.5 s.

An embodiment of the method further includes estimating the fundamental frequency of the infant cry further comprises validating, such that the estimate has an accuracy of at least about 80%, about 85%, about 90%, about 95%, or at least about 99%.

In an embodiment of the method, the computer readable format is a .csv file of values of the parameters of acoustic analysis.

An embodiment of the method further includes obtaining at least one parameter from normal infant subjects, and from infants having a developmental disorder or at risk for having a developmental disorder.

In an embodiment of the method, the developmental disorder is selected from the group of: Autism Spectrum Disorders selected from the group of: Autistic Disorder, Asperger's Disorder, Child Disintegrative Disorder, Retts Disorder, Pervasive Developmental Disorder NOS, and Autism Spectrum Disorder; Communication Disorders selected from the group of: developmental language disorders, Mixed Expressive-Receptive Language Disorder, Language Disorder, Speech Disorder, and Social Communication Disorder; Intellectual Developmental Disorders selected from the group of: Intellectual Developmental Disorder and Intellectual or Global Developmental Delay Not Elsewhere Classified; hearing impairment; cognitive impairment; language impairment; behavior disorders; and impairments or deficits related to "high risk" conditions exemplified by prenatal substance exposure, prematurity, low birthweight, intrauterine growth retardation, medical illness or brain injury, maternal history of mental illness, treatment, adverse pregnancy conditions exemplified by poor nutrition, poor prenatal care, physical assault, and genetic conditions that increase risk for cognitive, language, or behavioral impairments. An embodiment of the method further includes, after obtaining the digital recording of the infant cry, classifying or identifying a portion of infants that have the disorder from among a plurality of infants.

An embodiment of the method further includes, after obtaining the digital recording of the infant cry classifying retrospectively the portion of infants having the disorder, for example, the developmental disorder. A database of infant cries has been compiled including the cries of infants exposed to substance abuse, at risk of developmental disorders, etc., so that the retrospective analysis can be carried out to identify several distinguishing parameters so that prospective corrections are possible.

An embodiment of the method further includes, applying a pain stimulus to an infant, so that the pain stimulus stimulates the infant cry in reaction.

In an embodiment of the method, the infant cry is stimulated by applying a pain stimulus.

In an alternative embodiment of the method, the infant cry is spontaneous.

In an embodiment of the method, the method distinguishes a pain induced cry and a spontaneous cry.

An aspect of the invention herein provides an apparatus for analyzing an infant cry, the apparatus having the components,
  a recording device to record the infant cry, and so obtaining a digital signal of a recorded infant cry,
  a computer program embedded in a non-transitory computer readable medium to convert the digital signal of the recorded infant cry into a computer readable format, such that the computer program includes filtering the digital signal, estimating a fundamental frequency and a cepstrum value, smoothing the digital signal, eliminating outliers, extracting a confidence measure and applying a signal to noise ratio to the digital signal, and so obtaining a computer readable file, such that the computer readable file comprises at least one parameter of acoustic analysis of the recorded infant cry, and
  a computer, such that the recording device and the non-transitory computer readable medium are compatible with the computer and are linkable to the computer.

In an embodiment of the apparatus the parameter of acoustic analysis includes at least one of: frame number, time (ms), $F_0$, $F_0$ amplitude (dB), $F_0$ confidence [0-1], Hyper-pitch (Hz) ([1-5] kHz range), Hyper-pitch amplitude (dB), Hyper-pitch confidence [0-1], Peak pitch amplitude (dB), Overall amplitude (dB), Amplitude [0.5-10] kHz (dB), Amplitude [0-0.5] kHz (dB), Amplitude [0.5-1] kHz (dB), Amplitude [1-2.5] kHz (dB), Amplitude [2.5-5] kHz (dB), Amplitude [5-10] kHz (dB), $F_1$ (Hz), Amplitude of $F_1$ (dB), $F_2$ (Hz), Amplitude of $F_2$ (dB), $F_3$ (Hz), and amplitude of $F_3$ (dB).

In an embodiment of the apparatus, the computer readable format is a .csv file of values of the parameters of acoustic analysis.

In an embodiment of the apparatus, the recording device is a stand-alone device and the digital signal of the recorded infant cry from the recording device applied to the computer.

In an embodiment of the apparatus, the detection of the fundamental frequency of the infant cry further includes validating, wherein the estimate has an accuracy of at least about 80%, about 85%, about 90%, about 95%, or at least about 99%.

An embodiment of the apparatus further includes a stimulating component, wherein the stimulating component provides a pain stimulus to an infant and generates the infant cry in reaction.

In an embodiment of the apparatus, the recording device is a handheld device.

In an embodiment of the apparatus, the recording device is a mountable device, and is mounted adjacent to the infant to record the infant cry.

An aspect of the invention herein provides a device for stimulating pain in a subject and calibrating analysis of a pained utterance, the device having the components
- a striking arm, rotationally and movably attached to a platform,
- an intensity controller, mounted on the platform and digitally controlling intensity and propulsion of movement of the striking arm, and
- an initiating controller, such that the initiating controller is mounted on the platform and initiates a striking motion of the striking arm upon activation.

An embodiment of the device further includes an initiation signal coordinated with activation of the striking arm thus standardizing extent of stimulus and timing of a recording of a resultant utterance by the subject.

In an embodiment of the device, the initiation signal is emitted in audio range and includes a specific function for accurate time location such as a chirp and a frequency encoded coda containing information on strength of stimulus.

In an embodiment of the device, the device for stimulating pain is linked to a computer, wherein an activation of the striking motion of the striking arm is controlled by the computer.

An aspect of the invention herein provides an apparatus for infant cry analysis having the components of,
- means for receiving a digital sound recording or digitizing an analog sound recording of an infant cry, such that the sound recording is a consumer-device-formatted sound recording or other standard format,
- limiting the recording to a frequency range of about 200-2200 Hz representing a frequency band of interest and segmenting the recording into cry segments by type, such that the segment types include intervals of silence, short cries and long cries,
- performing computerized acoustic analysis on each segment to identify acoustic parameters of the recording, wherein the acoustic parameters include one or more of frame number, time (ms), $F_0$, $F_0$ amplitude (dB), $F_0$ confidence [0-1], Hyper-pitch (Hz) ([1-5] kHz range), Hyper-pitch amplitude (dB), Hyper-pitch confidence [0-1], Peak pitch amplitude (dB), Overall amplitude (dB), Amplitude [0.5-10] kHz (dB), Amplitude [0-0.5] kHz (dB), Amplitude [0.5-1] kHz (dB), Amplitude [1-2.5] kHz (dB), Amplitude [2.5-5] kHz (dB), Amplitude [5-10] kHz (dB), $F_1$ (Hz), Amplitude of $F_1$ (dB), $F_2$ (Hz), Amplitude of $F_2$ (dB), $F_3$ (Hz), and amplitude of $F_3$ (dB), and
- providing the detected parameters as a spreadsheet file for use as a validated medical or diagnostic record.

An embodiment of the apparatus further includes diagnostic software for highlighting diagnostic indicia among the reported parameters, such that the diagnostic indicia reflect likelihood that the infant cry indicates a developmental or neurological condition such as ASD, or a medical condition such as an airway or tissue anomaly.

An embodiment of the apparatus further includes a cry stimulus device for providing a controlled pain stimulus to an infant synchronized with recording of the infant's cry, and optionally further with a video recorder for validating cry data.

BRIEF DESCRIPTION OF THE DRAWINGS

These and other features of the invention will be understood from the description herein and the claims appended hereto, taken together with illustrative figures, wherein

DETAILED DESCRIPTION

Figure 1A:
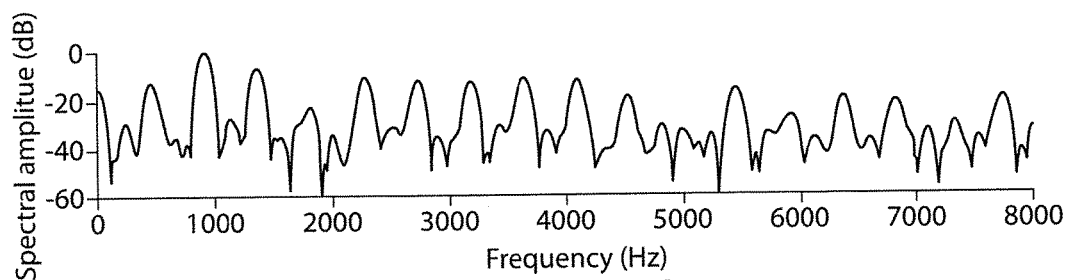
FIG. 1A shows an example of a voiced infant-cry spectrum.
Figure 1B:
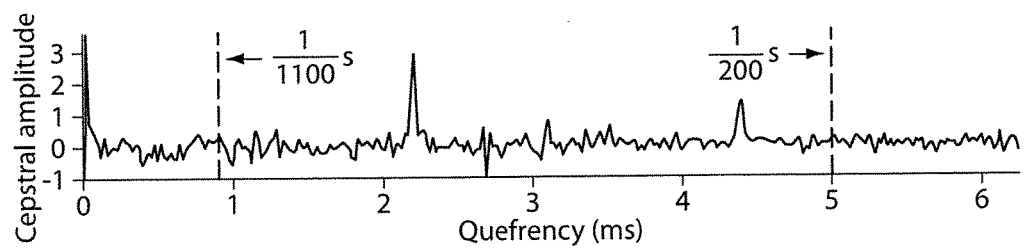
FIG. 1B shows a non-windowed cepstrum of same frame showing range for inspecting for rahmonics (the term "rahmonic" refers to harmonics in the cepstral domain)

Methods and results including working examples are found in the Appendix A (46 pages) of the United States provisional patent applications which are priority documents for this International Application, a then unpublished manuscript entitled "A Flexible Analysis Tool for the Quantitative Acoustic Assessment of Infant Cry", authors Brian Reggiannini, Stephen J. Sheinkopf, Harvey F. Silverman, Xiaoxue Li, and Barry M. Lester, and submitted to Journal of Speech, Language, and Hearing Research, and currently available online as Journal of Speech, Language and Hearing Research 2013: doi:10.1044/1092-4388(2013/11-0298) hereby incorporated by reference in its entirety herein. Briefly as described therein a versatile, sensitive and accurate method and apparatus for infant cry analysis is described together with its use to measure, detect and quantify cry features of clinical interest.

Methods and Apparatus: System Description and Approach

The acoustic analyzer herein described was specifically designed and configured for infant-cry analysis, utilizing signal processing algorithms arranged to extract acoustic parameters describing infant cries from standard digital audio files. The analysis device uses a frame rate of 25 ms with a frame advance of 12.5 ms and applies Cepstral-based acoustic analysis, and it proceeds in two phases, computing frame-level data and then organizing and summarizing this information within cry utterances. The system was automated to detect features of interest under controlled or accurate recording conditions, for features which were known or suspected to be diagnostic indicators.

Accuracy of the automated system was evaluated by comparing determinations of voicing and fundamental frequency ($F_0$) to voiced segments and pitch periods manually coded from spectrogram displays. The system was found to detect $F_0$ with 88% to 95% accuracy, depending on tolerances set at 10 Hz to 20 Hz, and Receiver Operating Characteristic (ROC) analyses demonstrated very high accuracy at detecting voicing characteristics in the cry samples. The digitized signal processing of the automated infant cry analyzer provides high sensitivity and accuracy for detection of important acoustic features of infant cry, as well as identification of new features or significant combinations of such features in known populations. A unique and important aspect of this work is the rigorous testing of the system's accuracy as compared to ground truth manual coding. The analyzer system has many implications for basic and applied research on infant cry development, including embodiment in instruments, early in-clinic detection of conditions, confirming, diagnosing or tracking development or changes in conditions, and preparation of objective medical records for subject files.

Processing in the cry analysis tool utilizes robust methods for voicing determination along with a cepstral analysis for the detection and tracking of $F_0$. Investigating the validity of automated acoustic assessment of cry can be thought of as studying the sensitivity and specificity of an automated method of detecting the signal periodicity that constitutes $F_0$. The tool extracts acoustic information from digitally recorded infant cries. The sensitivity and specificity of the automated system to detect $F_0$ (pitch periods) is automatic and fast, and compares favorably to the pitch periods manually coded by a trained observer from a sound spectrogram (oscilloscope view). Additional processing may categorize voiced versus typically short, unvoiced utterances, or segments of utterances that are unvoiced. This includes a quantification of the confidence of the voicing determination, which can be adapted by researchers depending on the scientific questions being addressed. The detailed output from this system can be easily subjected to statistical analysis for hypothesis testing. This system is detailed and flexible enough to allow researchers to describe infant cries at the utterance level, while also producing detailed frame-by-frame acoustic output.

Scope of input data and the signal processing stages were determined based upon the range of measures or outputs to be examined, basing this list on prior cry analysis work. These included parameters to characterize $F_0$, amplitude or energy of cry, timing variables (latency, onset, duration, inter-utterance interval, etc.) and formants (while acknowledging difficulty in measurement). In addition to the kinds of variables used in prior automated analyses, a further aim was to use $F_0$ tracking to model the shape or contour of $F_0$ across each cry utterance in a cry episode. This may be analogized to "cry melody" in some past research, such Wermke, Leising, and Stellzig-Eisenhauer (2007) cited above, where $F_0$ was characterized as rising then falling, or having other contours across a cry utterance.

The complex interplay of neural, physiological and anatomical factors manifested in the properties of the driving function of the cry was considered, notably, periodicity of the glottal motions which determine properties such as the pitch or the amount of voicing-excited turbulence in a cry. The shape of the vocal tract determines the resonant frequencies (formants) of the spectrum of the cry at a given instant. Important acoustic properties of infant cry include $F_0$, defined as the fundamental frequency of the glottal excitation (vibrations of the vocal folds), and the formant frequencies, defined as resonances of the vocal tract. In other or further systems, non-vocal-fold driven turbulences need also to be detected and categorized in a suitable analysis system.

Processing in the proof-of-principle system is run as two sequential programs: Phase I analyzes the digitized data to produce a set of parameters for each consecutive 12.5 ms frame. Phase II takes the Phase I output as input and produces an output record for each consecutive group of frames that has similar properties. The analysis tool is currently implemented in MATLAB®, but is easily adaptable for any embedded processor. The analyzer assumes the standard 16-bit, 48 ks/s digital (768 kbits/s) .wav file of a consumer or professional digital sound recorder as the cry recording upon which it operates. These sampling and quantization parameters are sufficiently high to ensure that all cues are captured and that there is sufficient headroom for dynamic range differences. In this study, we have recorded cry samples using an Olympus DM-520 digital voice recorder (Olympus Imaging America, Inc., Center Valley, Pa.). This standardized input format can easily be replicated in other studies, and the system processing may be carried out in a suitably programmed general purpose computer, or in a customized device adapted to receive and process the digital recording.

Phase I of the processing takes the .wav files and produces a comma-separated value (CSV) file that is not only readable by the Phase II program but also by programs such as Microsoft Excel. In the first phase of the analysis system, all outputs relate to the unit of a fixed length, fixed-advance frame described by 22 numerical parameters. Thus, as each number has a 32-bit representation, this implies a data rate of only 56.32 kbits/s, a significant reduction. The first two lines of each Phase I output file are headers. The fields for the header record are defined in TABLE 1.

TABLE 1

Initial header record definitions

1: Phase I or Phase II (text)
2: Subject (text)
3: Subject description (text)
4: Number of zero frames
5: Mean value of recording [0, 32767]
6: 1% Dynamic range [0, 32767]
7: 1% Dynamic range (dB)
8: 5% Dynamic range [0, 32767]
9: 5% Dynamic range (dB)
10: 10% Dynamic range [0, 32767]
11: 10% Dynamic range (dB)
12: Quality class One area addressed by the system is that there are many useful (older) infant-cry samples that have been recorded on analog tape. However, recording quality of these tapes may vary. Thus a preliminary automatic scan of a digitized recording has been designed to ascertain a recording's quality, based on background noise—usually hum and signal-to-noise ratio (as determined by an average amplitude for high-energy events to the amplitude of easily identifiable "silence" regions)—and a detection of saturation at some phase of the recording process. The mean value of the recording, an estimate of the dynamic range, and a classification of the quality of the file (high-quality, noisy, low-level, analog saturated, digital saturated) are all put into the header file for the Phase I system.

The rest of the output file consists of fixed-length records, one record per frame, as defined in TABLE 2. A fixed frame rate of 1200 samples (25 ms) was used with a frame advance of 600 samples (12.5 ms) to keep reasonably high resolution in both time and frequency. The analysis system was designed to be liberal with its use of computation so as to reflect resultant parameters more accurately. Thus three discrete Fourier transforms are computed for each 1200-point frame. The middle 768 points are transformed for the $F_0$ estimate as explained below. The full frame (1200 points) is transformed for amplitude computations and an interpolated transform of 4096 points (1448 zeros, the 1200 point frame and 1448 zeros) is used to detect $F_0$ above 1 kHz (what we term hyper-pitch).

TABLE 2

Phase I: Definition of fields of per frame record

1: Frame number
2: Time(ms)
3: $F_0$(Hz)
4: $F_0$ amplitude(dB)
5: $F_0$ confidence [0, 1]
6: Hyper-pitch(Hz) ([1, 5]kHz range)
7: Hyper-pitch amplitude(dB)
8: Hyper-pitch confidence [0, 1]
9: Peak pitch amplitude(dB)
10: Overall amplitude(dB)
11: Amplitude[0.5, 10]kHz(dB)
12: Amplitude[0, 0.5]kHz(dB)
13: Amplitude[0.5, 1]kHz(dB)
14: Amplitude[1, 2.5]kHz(dB)
15: Amplitude[2.5, 5]kHz(dB)
16: Amplitude[5, 10]kHz(dB)
17: $F_1$(Hz)
18: Amplitude of $F_1$(dB)
19: $F_2$(Hz)
20: Amplitude of $F_2$(dB)
21: $F_3$(Hz)
22: Amplitude of $F_3$(dB)

The Phase II program takes the Phase I data as input and reduces the data further, separating it into groups of frames having similar properties, which we call sound segments. The CSV output has a record for each of these groups of frames. The concatenated groups of frames are labeled to be one of the following classes:
 1. silence
 2. short utterances (length<0.5 s, relatively high energy)
 3. long utterances (length>0.5 s, high energy)
The output from Phase II contains information summarizing utterance-level characteristics of infant cries, and the Phase II output is expected to be most useful for studies of crying in various infant populations. Phase I accuracy has been carefully tested because the validity of the summary output rests upon this phase.

The Phase I System

There are several approaches that could be used for pitch detection, and the more common of these methods are based on:
 1) time-event rate detection (Ananthapadmanabha & Yegnanarayana, 1975; Rader, 1964; Smith, 1954, 1957);
 2) auto-correlation methods (Dubnowski, Schafer, & Rabiner, 1976; Gill, 1959; Rabiner, 1977; Stone & White, 1963); and
 3) frequency domain methods.
Time-event rate detection methods are based on the fact that if an event is periodic, then there are extractable time-repeating events that can be counted and the number of these events per second is inversely related to the frequency. Auto-correlation methods are used as a measure of the consistency or sameness of a signal with itself at different time delays; the peak of the time-delay value is returned as the pitch period. Finally, frequency domain approaches include methods such as comb filters (filters in which a signal is subtracted from itself at different time delay values) (Martin, 1981), tunable infinite impulse response (IIR) filters (Baronin & Kushtuev, 1971), and cepstrum analysis (Bogert, Healy, & Tukey, 1963; Noll, 1967).

The time-event rate detection methods are extremely simple and easy to implement. However, they have immense difficulties dealing with spectrally complex signals such as human speech or a baby's cry. The autocorrelation and the first two frequency domain methods are also more suitable for cleaner signals (e.g., sounds produced by musical instruments). Perhaps the method most widely used for obtaining $F_0$ in adult speech is cepstrum analysis. When applied correctly, it has proven to be a robust method for describing acoustic properties of non-infant vocalizations, and if suitable for the complex vocalic signals of infant cry, would be useful; the resulting cepstral coefficients are the standard features for speech recognition algorithms. We selected cepstrum analysis to develop the cry analysis algorithm in this project.

It is accepted that a normal infant cry $F_0$-range is 200 Hz to 1 kHz or a pitch period range of 5 ms to 1 ms. As pitch-period estimates are obtained using a modified version of the cepstrum method (Noll, 1967), several pitch periods are required within each frame to make the short time frame appear periodic. Thus, to get a minimum of three pitch periods (and a reasonable number for applying a fast Fourier transform of FFT) we selected a fixed frame of 768 points (or 16 ms for 48 kHz sampling) of each 1200-point frame and a 768-point Hamming window. A larger window will cause the cepstral pitch peak to broaden for the higher $F_0$ values, and a smaller window will not have as good cepstral peaks for low values of $F_0$. The Hamming window will broaden the harmonic peaks, but eliminate most the effects due to sidelobe accumulations. This analysis strategy was decided upon in order to capture 4 to 8 pitch periods per frame.

Figure 1C:
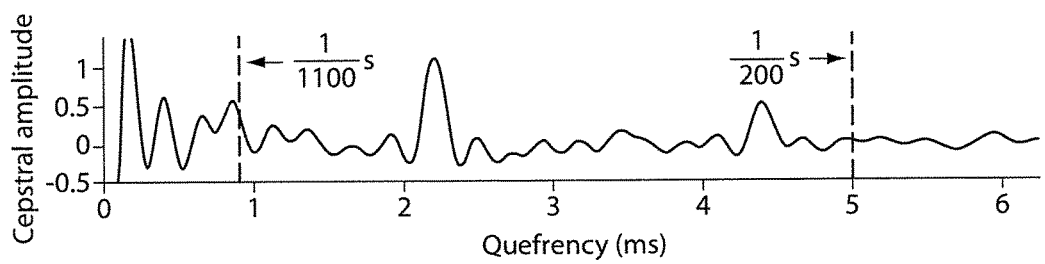
FIG. 1C shows a windowed cepstrum showing range for inspecting rahmonics.

Given the nature of infant cry, greater frame lengths would decrease the reliability of pitch-period estimation. Thus, we had to modify the basic technique in order to compensate for the unique characteristics of infant cry. The first change was to apply a frequency window W [r], effectively limiting the band to be considered to be from 200 Hz to 2200 Hz, to the log-spectrum before computing the inverse DFT. Because energy in voiced speech naturally falls off after 4 kHz, the spectral harmonic structure is amplitude modulated by the rolloff function, which can cause multiple peaks in the cepstrum when the sampling rate exceeds 8 kHz. Applying a frequency window smoothes the cepstrum, eliminating these modulation effects. The window also deemphasizes low- and high-frequency noise. The effects of the frequency window are depicted in FIG. 1C in which the pitch period is easy to identify, although a second rahmonic is also evident.

We note that infants generally do not double or halve their pitch frequency nearly instantaneously, during voiced portions of a cry vocalization. Thus, by considering multiple frames at once, many $F_0$ doubling and halving estimation errors can be eliminated. We consider halving and doubling "errors' to be those that occur for one or two frames, which would imply very rapid changes in pitch frequency. It is these that we try to eliminate, not the longer doubling or halving regions that appear when even or odd harmonics disappear in the spectrogram. A dynamic-programming smoother is a reasonable mechanism to ensure continuity in the $F_0$ estimates at transitions and many other anomalies. This is not a new idea (Secrest & Doddington, 1982), but here the implementation is specifically set-up for infant cries. In our implementation, 50-frame blocks (0.625 s) are run through the dynamic-programming algorithm after determining $F_0$ and a confidence measure for independent frames. The last 50 frames of the recorded cry constitute the last block. As the number of frames is not likely to be divisible by 50, there is some special processing due to overlap for the last block. All negative cepstral values are truncated to zero and the accumulated path metric is simply the sum of the 50 cepstral values built in the normal forward part of the dynamic-programming algorithm. The pitch period is allowed to change no more than plus or minus 20 cepstral points (0.416 ms) per frame. The backtracked path is used for the initial estimates for $F_0$. Following the dynamic programming, some further outliers (typically at utterance transitions) are eliminated using a standard 5-point median filter. The result is pitch period estimate $q_0[i]$ for frame i, and pitch frequency (Data element 3 in TABLE 2 above) is simply $F_0[i]=f_s/q_0[i]$.

Data element 4, pitch energy, is the cepstral value of $q_0[i]$, $C[q_0[i], i]$.

Instead of using amplitude alone, the pitch estimation system is also well suited for making voicing decisions for each frame. Data element 5 in Table 2 is a pseudo-probability for voicing based on the cepstral analysis. For cepstrum $C[q, i]$ and pitch-period estimate $q_0[i]$, the traditional cepstrum method uses $C[q_0[i]]$ as a measure of voicing. This measure will fluctuate under different noise conditions, making it difficult to find a reliable threshold for a multi-environment system. Instead, we use a signal-to-noise ratio (SNR)-like measure to make a voicing decision. This measure is based on the height of the cepstral peak with respect to the cepstrum noise level. The window $W[r]$ effectively smoothes the cepstrum of length N by a factor of D, where:

$$D \equiv \frac{N}{\sum_{r=0}^{N-1} W[r]} \quad (1)$$

This smoothing causes peaks in the cepstrum to have a width of approximately D+1 samples. This information is used to compute the voicing confidence measure V which is a function of $C[q_0[i], i]$ and its surrounding. The cepstrum method searches for evidence of periodicity within a finite pitch-period range based on knowledge of human $F_0$ production. In this method, $q_{min}$ and $q_{max}$ are the minimum and maximum pitch-period (quefrency) indices in the search region. These are fixed and do not vary with the frame index i. The voicing-detection algorithm begins by zeroing out all negative $C[q]$ values and all values outside the region $q \in [q_{min}, q_{max}]$ in the cepstrum $C[q, i]$. This non-negative cepstrum is denoted as $\hat{C}[q, i]$, and let $\hat{D}=\frac{1}{2}D$ &. Pitch-period estimate $q_0[i]$ is chosen to correspond to the maximum value of $\hat{C}[q, i]$, as is done in the traditional method. Then, the voicing confidence $V[q_0[i], i]$ is defined as, $$V[q_0[i], i] = \frac{\sum_{r=1}^{R} \sum_{i=\hat{D}}^{\hat{D}} (\hat{C}[r \cdot q_0[i], i])^2}{\sum_{j=q_{min}}^{q_{max}} (\hat{C}[j, 1])^2} \quad (2)$$

where R is the number of rahmonics to include. It was found that R=3 was sufficient, as larger rahmonics were often insignificantly small.

$V[q_0[i], i]$ is a number between 0 and 1. Values of $V[q_0[i], i]$ corresponding to high-quefrency (low-frequency) pitch-period estimates tend to have smaller magnitudes because fewer rahmonics fall within the search interval $[q_{min}, q_{max}]$. The decision threshold, $\alpha[q_0[i]]$, depends linearly (from 0.7 at $q_{min}$ to 0.5 at $q_{max}$) on the index of the current pitch-period estimate $q_0[i]$. In the Phase II program a frame would be labeled as voiced if $V[q_0[i], i] \geq \alpha[q_0]$ perhaps along with some amplitude criteria.

$$\alpha[q_0] \equiv \frac{0.2}{q_{max} - q_{min}} (q_{min} - q_0) + 0.7 \quad (3)$$

In addition to being more robust to different noise conditions, $V[q_0[i], i]$ also protects against doubling errors by including the magnitude of cepstral content away from the peak. Although doubling errors will not be corrected by using this method, it was ultimately found that ignoring such difficult frames by labeling them unvoiced was sufficient for the task at hand.

Figure 2:
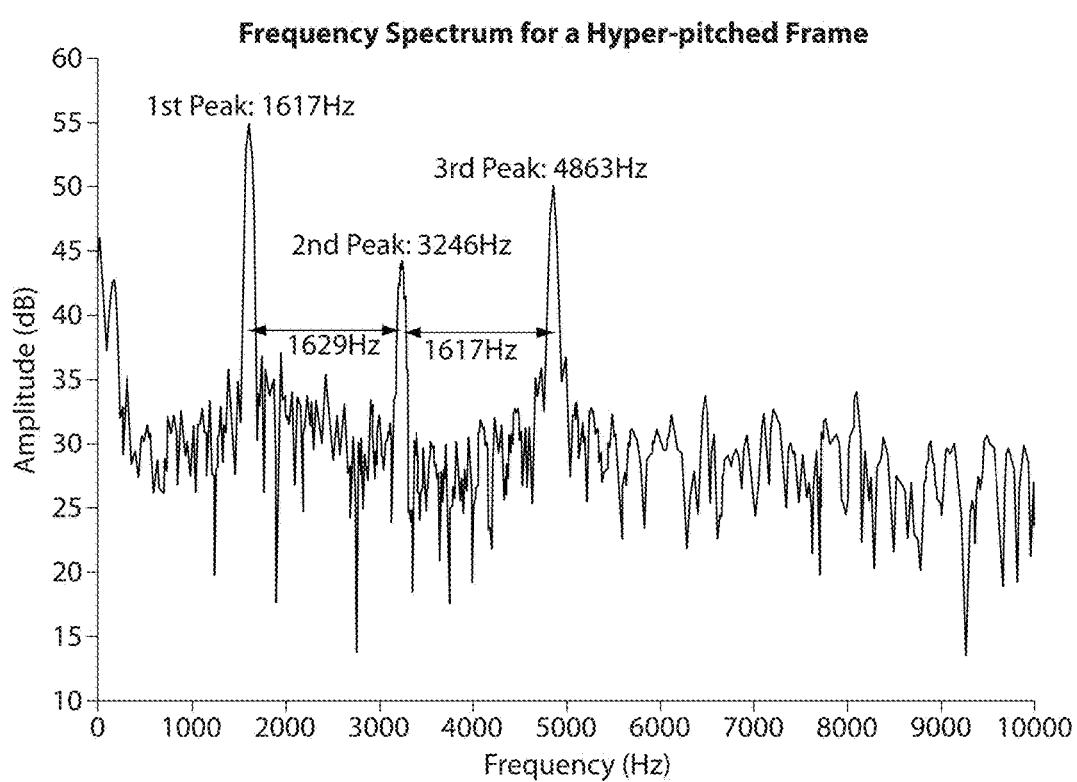
FIG. 2 shows an example of the spectrum of a hyper-pitch-excited frame and the cues from the peaks.

One potentially significant mode in an infant's cry is when the fundamental frequency is above 1000 Hz, which we call hyper-pitch (Golub, 1989; LaGasse et al., 2005). The method herein thus attempts to determine a set of hyper-pitch values for each frame. This is done using a Hamming-windowed 4096-point DFT with the full 1200-point frame data in the center of inserted zeros to compute an interpolated spectrum, and search its log-magnitude for peaks in the range from 1000 Hz to 5000 Hz. The highest peak P[1] in the range is found first and, as the lowest hyper-pitch is 1000 Hz, the spectrum is masked from max[1000, P[1, i]−1000] to min[5000, P[1, i]+1000] and searched for another peak. This process is repeated until three such peaks have been found P[k, i], where k denotes the individual elements of the set of three peaks ($k \in [1, 3]$). The set is then reordered to be left-to-right as $\hat{P}[k, i]$. It is hypothesized that the three peaks form some harmonic set and the frequency differences are taken yielding a hyper-pitch value $F_{hp}[i]=0.5(\hat{P}[3,i]-\hat{P}[1, i])$. If only two peaks can be found, then $F_{hp}[i]=\hat{P}[2, i]-\hat{P}[1, i]$. There is a special case when the hyper-pitch is about 1000 Hz and the odd harmonics dominate. In this case, the minimum difference between peaks is taken as the hyper-pitch frequency. An example of a spectrum for a frame driven by hyper-pitch is shown in FIG. 2.

The hyper-pitch energy (seventh value in the record) is simply taken as the average of the fundamental hyper-pitch value and two of its harmonics. It is not necessarily that of the average of the peaks. The hyper-pitch confidence (eighth value in the record) is determined in a similar fashion to that of the confidence in the normal pitch range. It is a number between zero and one that correlates well with the validity of the hyper-pitch condition being active in the frame. For this result the power, A,—not the log power—is accumulated for the range 1000 Hz→5000 Hz and the power in the detected peaks, B, (up to four in the range) is also accumulated. The power for a given peak is accumulated over about 30 interpolated points or about 360 Hz about the peak. The ratio B/A is the confidence measure.

Fields 10 to 16 of the record give the amplitudes in dB for the entire band and for the six sub-bands listed above. The full Hamming-windowed 1200-point DFT output is used to accumulate the power in each prescribed band (and overall). Those values are directly converted to dB without any normalization. Thus no information is lost, but differences in recording levels, distance from the microphone, and other aspects of sound acquisition will also affect these data.

However, keeping un-normalized data allows the Phase II system to consider the recording conditions when making its decisions.

As noted, the determination of formants is a very difficult problem for infant cries due to the high pitch of the cries and thus the sparse harmonics. Formant positions can be estimated, but their precise central values, if somewhat distant from a pitch harmonic, may be hard to obtain. To estimate formants as accurately as possible, we use the interpolated 4096-point DFT data. After obtaining the log-magnitude spectral data, we apply a low pass "lifter" to the data whose parameters depend upon the pitch value. Then substantial peaks in the smoothed data are taken for the formant positions and the heights of the peaks are taken for the magnitudes.

Figure 3A:
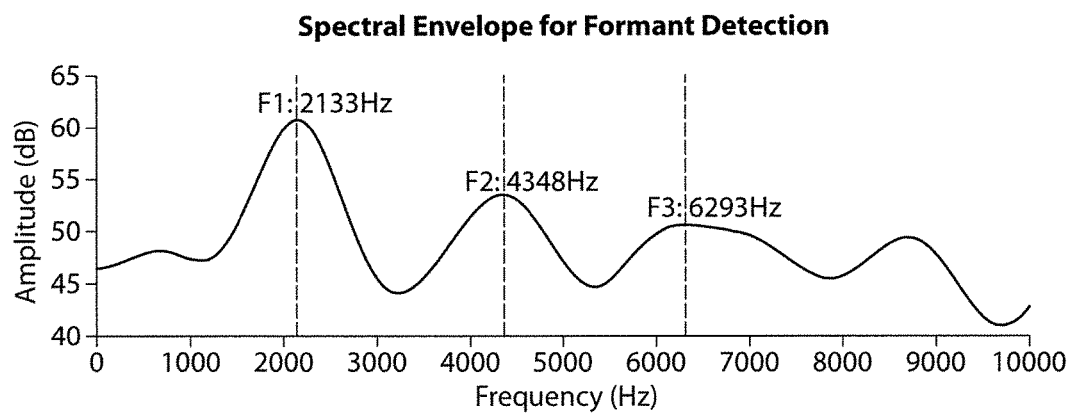
FIGS. 3A and 3B show an example of the smoothed function for determination of formant positions, evidencing is strong influence from the harmonics of $F_0$.
Figure 3B:
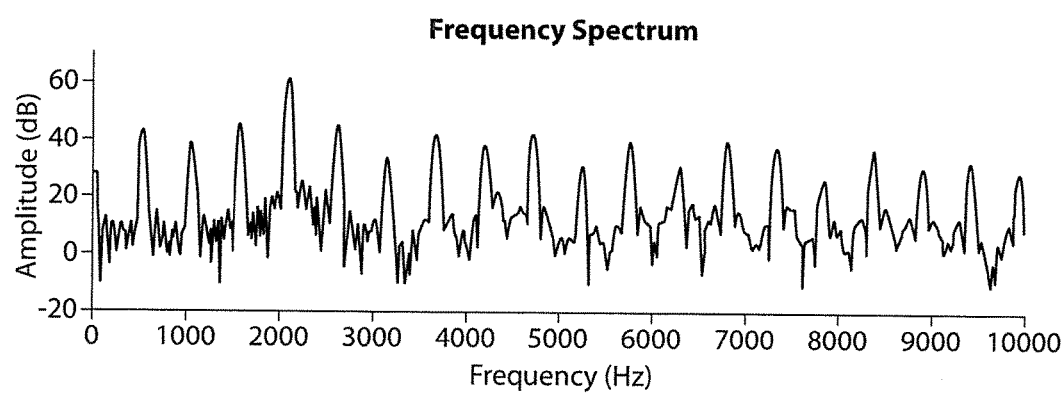

FIGS. 3A and 3B show a typical voiced frame. In FIG. 3A the smoothed spectrum is shown while in FIG. 3B the unsmoothed spectrum is given. The formant positions and their magnitudes take up the last six positions in each record. One should note that the third formant is more arbitrary than the first two.

Phase II

The Phase II stage of the analyzer is here described briefly. Phase II output starts with two header records, the first being the same one as the Phase I header with the first field changed to read "Phase II". The second contains 81 Phase II column headings. Specific definitions of the fields appear in TABLE 5.

TABLE 5

Phase II: Definition of fields of per-utterance record

1: File name
2: Start Frame
3: End Frame
4: Length(frames)
5: Length(ms)
6: Class label
7: Time from prev. utt.(ms)
8: # short Utt between utt
9: # frames with no $F_0$
10: # voiced fric. frames
11: Frac. voiced fric frames
12: Classify "1" if voiced fric. > 60%
13: Start frame of longest voiced fric.
14: End frame of longest voiced fric.
15: # frames with $F_0$
16: Avg. $F_0$(Hz)
17: Max. $F_0$(Hz)
18: Min. $F_0$(Hz)
19: STD of $F_0$ (Hz)
20: # Hyper-pitch Frames
21: Avg. Hyper-pitch
22: Max hyper-pitch
23: Min hyper-pitch
24: STD of hyper-pitch
25: Avg. $F_0$ peak val
26: Avg. hyper-pitch peak val
27: Avg. $F_1$(Hz)
28: Max of $F_1$(dB)
29: Min of $F_1$(dB)
30: STD $F_1$ (Hz)
31: Avg. $F_2$(Hz)
32: Max $F_2$(Hz)
33: Min. $F_2$(Hz)
34: STD $F_2$ (Hz)
35: Avg. $F_3$(Hz)
36: Max. $F_3$(Hz)
37: Min. $F_3$(Hz)
38: STD $F_3$ (Hz)
39: Opt. polyfit order
40: Real order of polyfit
41: Polyfit coeff of order 0
42: Polyfit coeff of order 1

TABLE 5-continued

Phase II: Definition of fields of per-utterance record

43: Polyfit coeff of order 2
44: Polyfit coeff of order 3
45: Polyfit coeff of order 4
46: Polyfit Coeff of order 5
47: Max of polyfit (fract of utt time)
48: Max of polyfit (Hz)
49: Min of polyfit (fract of utt time)
50: Min of polyfit (Hz)
51: Polyfit class(see Table 5)
52: Class = '1' if final "ripple"
53: Err. polyfit
54: Avg Amplitude(dB)
55: Peak Amplitude(dB)
56: Min. Amplitude(dB)
57: STD Amplitude(dB)
58: Avg Amp [0.5, 10]kHz (dB)
59: Peak Amp [0.5, 10]kHz(dB)
60: Min Amp [0.5, 10]kHz(dB)
61: STD Amp [0.5, 10]kHz(dB)
62: Avg Amp[0, 0.5]kHz(dB)
63: Peak amp [0, 0.5]kHz(dB)
64: Min Amp [0, 0.5]kHz(dB)
65: STD Amp [0, 0.5]kHz(dB)
66: Avg Amp [0.5, 1]kHz(dB)
67: Peak Amp [0.5, 1]kHz(dB)
68: Min Amp [0.5, 1]kHz(dB)
69: STD Amp [0.5, 1]kHz(dB)
70: Avg Amp [1, 2.5]kHz(dB)
71: Peak Amp [1, 2.5]kHz(dB)
72: Min Amp [1, 2.5]kHz(dB)
73: STD Amp [1, 2.5]kHz(dB)
74: Avg Amp [2.5, 5]kHz(dB)
75: Peak Amp [2.5, 5]kHz(dB)
76: Min Amp [2.5, 5]kHz(dB)
77: STD Amp [2.5, 5]kHz(dB)
78: Avg Amp [5, 10]kHz(dB)
79: Peak Amp [5, 10]kHz(dB)
80: Min Amp [5, 10]kHz(dB)
81: STD Amp [5, 10]kHz(dB)

The first step in the Phase II processing utilizes the recording quality classification that is contained in the header information from the Phase I pre-scan. When running Phase II, the user defines which quality classes should be used, and Phase II processing is then performed only on recordings with quality classifications that have been entered by the user. The Phase II data output consists of records each of which describe a sound-segment, where a sound-segment is a group of consecutive frames that are similar. The Phase II analyzer takes in the Phase I data and produces an output .csv file with sound-segment records of size 81 and an average rate of about three sound-segments per second. Thus the data rate, using 32-bit numbers, is reduced by a factor of about 7 to 7776 b/sec. In Phase II, the processing makes decisions, the most fundamental of which have to do with the partitioning the cry into these utterances.

The output contains one 81-element record for each of the three sound-segment types that were defined previously, long-utterance, short-utterance, and silence. The specific field definitions are available in the supplementary material (see above). All 81 fields are filled for long utterances, and appropriate fields filled for the other types. The 81 fields quantify file ID and 5 various classifier outputs, 8 timing parameters, 6 $F_0$ parameters, 5 hyper-pitch parameters, 13 formant parameters, 15 parameters from fitting a polynomial to the pitch contour, and 28 parameters for amplitudes from several octave frequency bands. The segmentation is obtained by K-means clustering the 500 Hz to 10 k Hz amplitude (dB) data into three classes in a pre-scan of the whole recording and using the results to classify each frame as one of three classes: "1"=low energy, "2"=transition energy, and "3"=high energy. The important long utterances consist of a contiguous sequence of frames that each have a 500 Hz to 10 kHz amplitude (dB) classified as in the high-energy cluster with a high $F_0$ confidence. Using these frame labels, the change in energy to help with the boundaries, and some extension rules, the partitioning is determined. If a contiguous sequence of high-energy frames is longer that 0.5 seconds (40 frames), a long utterance is created. If only the length criterion is not met, then that sequence is classified as a short utterance, and if the sequence is of low energy, then the sequence is called a silence. The operational definition of a long utterance is consistent with prior research on infant crying (LaGasse et al, 2005), and allows for analyses of utterances produced in different types of cries (e.g., initial utterances of pain-induced cries can be expected to be longer than 0.5 seconds, but cry utterances produced in different contexts may be shorter). In our work with sound files of adequate quality, there has been virtually no mislabeling of low-energy cry information as silence.

An important characteristic of many infant cries is when the cry is very intensive with large amount of frication in the high-energy long utterances. This can be found in our system by seeing if there is very high energy for a frame, but low $F_0$ confidence. What happens is that the extra frication-sounding energy for this frame tends to mask the cepstral detector. We call this phenomenon voiced frication and extract pertinent information about it for the Phase II output. Also, many infants exhibit a short air-intake noise—audible inspiration which typically follows a long cry and/or one produced by an infant under duress—immediately after a long utterance. If sufficiently close (in time) to the end of a long utterance, this period is included in the long utterance but specifically noted as a classifier for the long utterance. An audible inspiration of this type is likely to be perceived as a part of the cry utterance. The use of this classifier retains the full length of the utterance, while also allowing for the user to examine utterances with this classifier separately. While the third formant is very suspect, it has been included. As the contours of the $F_0$ data within an utterance are important, we approximate these contours by a polynomial fit. Using an information-theoretic criterion, we estimate the "best" order to use for this model. This number is often large, approaching 20 or more. We then restrict the fit to be of order five or fewer, and the best fit is often of the third or fourth order. All the polynomial-fitting is done on the $F_0$ data. The class field is a number (1 to 10) descriptor of the shape of the fit, e.g., rising, falling, flat, double peak etc. The final 28 fields contain information on the amplitudes. Again, these values have not been normalized in any way. Each of the sound-segment-level statistics has been calculated by going back to the power domain, accumulating properly over the frames of an utterance, and then transforming back to dB.

Validation of Pitch-Estimation and Frame Voicing-Decision Algorithms

Interpreted results from older analysis systems most often indicate that timing—lengths and spacing of utterances—fundamental frequency and voicing are highly informative features of infant cry production. Moreover, other features of infant cry, such as the contours of $F_0$ across utterances, are dependent on the accuracy of $F_0$ estimation. Therefore, an experiment was conducted to evaluate the performance of the voicing-detection and pitch-estimation algorithm. We identified cry recordings recorded previously in an ongoing longitudinal study (Lester et al., 2002). Cries were elicited and recorded using procedures approved by hospital Institutional Review Board (IRB). The IRB also approved access to these archival recordings for the purpose of the analyses reported in this paper. Recordings were made of cries elicited by standard methods (LaGasse et al., 2005) from typically developing infants at one month of age. Cries were elicited by a specially designed device that applied a pain stimulus (analogous to a rubber-band snap) the sole of the right foot while babies lay supine in a pram with a unidirectional microphone suspended at a standardized distance above the baby (5 inches). Cry samples were selected from an existing longitudinal dataset. A total of 15 cries from 15 individual babies were evaluated, each containing between 36 and 42 seconds of cry data. We coded and analyzed only cries characterized by intense, loud, rhythmic, and sustained vocalizations that are differentiated from brief cries and fusses characteristic lower states of arousal.

These cries were selected on basis of the infants being the products of full term normal pregnancies and within normal limits scores on later assessments of developmental functioning (e.g., Bayley Scales of Infant and Toddler Development at 24 months of age). Recordings were made in a quiet and controlled setting at a hospital-based developmental assessment center, and thus the recording quality was high and background noise was minimal. Recordings were sampled at 48 kHz with the Olympus direct PCM recorder described above.

Establishing Ground Truth

Ground truth was established for both the presence of voicing and the corresponding $F_0$ by hand-labeling each cry. Pitch-frequency labels were obtained by hand-marking pitch-period intervals from the time-domain plot of the cry waveform. For this purpose we utilized a software program developed in our lab that conveniently displays both time and frequency plots from .wav files (Silverman, 2011). All labels were affixed by a single person, trained to affix time markers at the high-energy peaks that generally allow the denotation of a pitch frequency. Pitch-period labels were affixed for regions of each cry recording determined to be clearly voiced.

Figure 4:
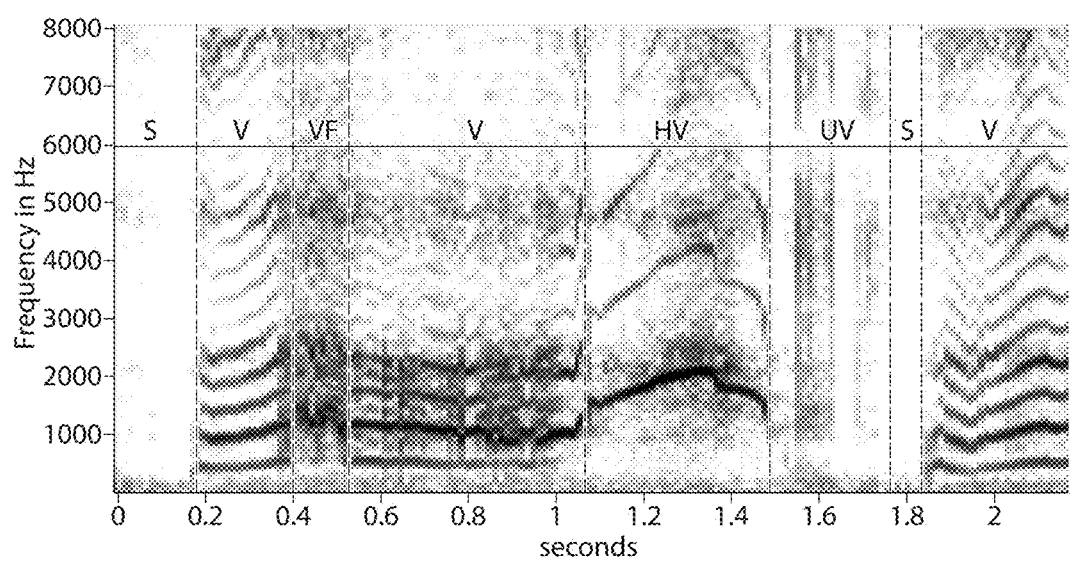
FIG. 4 illustrates a spectrogram plot hand-labeled to establish ground truth for voicing type; intervals were labeled as voiced (V), unvoiced (UV), silence (S), voiced-fricative (VF), or high-voicing (HV)

The intervals of voicing were also hand-labeled using a spectrogram plot, as shown in FIG. 4. Intervals were first marked at the frame level, indicating that the region about that particular 12.5 ms frame advance was voiced. Then, the regions indicated by the labels on the frames as voiced were fine-tuned to indicate specific interval types at the resolution of the sampling time by viewing the corresponding time-domain plot. Five different interval types were defined: voiced (V), unvoiced (UV), silence (S), voiced-frication (VF), or high-voicing (HV). An interval was labeled as voiced (V) if the spectrogram showed a well-defined harmonic structure, indicating periodicity. An interval was labeled as unvoiced (UV) if the spectrogram showed significant energy without the presence of harmonics. Silence (S) intervals showed very low signal energy. The voiced-frication (VF) label was assigned when an interval exhibited a harmonic structure in addition to turbulent (frication) noise at non-harmonic frequencies. Voiced-frications were given a separate label because it is unclear whether such frames should be labeled as voiced or unvoiced. Finally, the high-voicing (HV) label was assigned to intervals with a very sparse harmonic structure, indicating a very high fundamental frequency (greater than 1 kHz) which we have called hyper-pitch excited frames.

TABLE 3 shows the number of frames in the data set corresponding to each of the five voicing classes. The infant cries in this data set consisted mainly of voiced speech. Examples of the HV and UV classes occurred quite infrequently.

TABLE 3

Number of frames in the data set labeled with each of the five voicing classes

| Voicing Class | # of Frames |
|---|---|
| Voiced (V) | 27745 |
| High-Voiced (HV) | 92 |
| Unvoiced (UV) | 3155 |
| Voiced Frication (VF) | 560 |
| Silence (S) | 13638 |

Figure 5A:
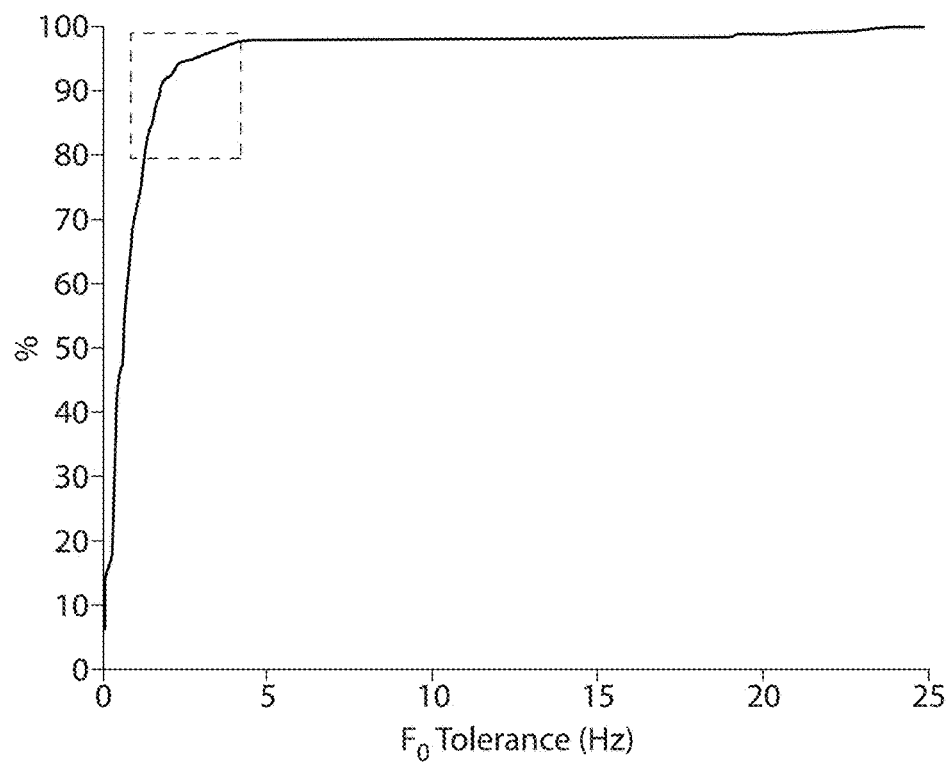
FIG. 5A shows Receiver Operating Characteristic (ROC) Curve showing agreement between ground-truth hand-labeling and manual hand-labeling of about 10% of data used in the validation.
Figure 5B:
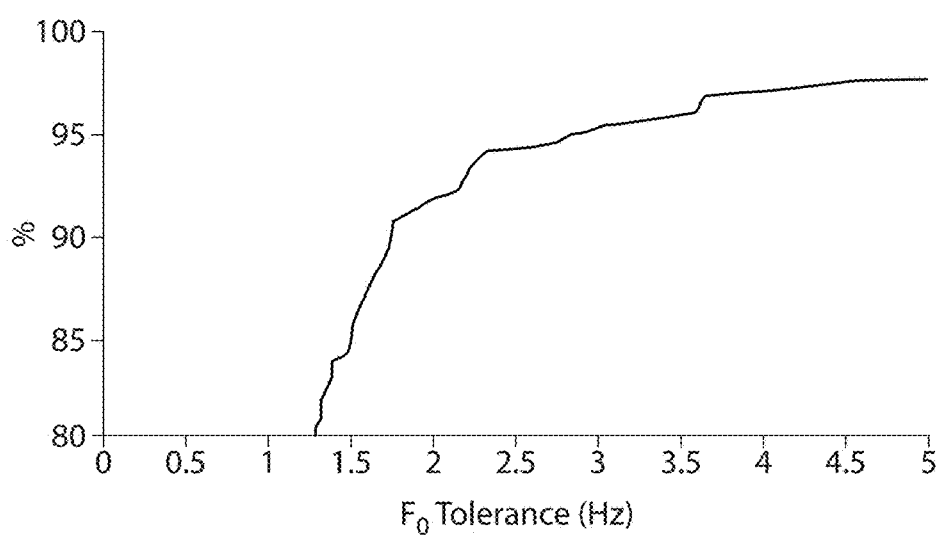
FIG. 5B shows an expanded graph of the dotted area of FIG. 5A.

The labeling was conducted by a research assistant who was first trained to understand the kinds of patterns that should be labeled, and who was then trained to criterion-level of accuracy by Brian Reggiannini. Once the labeler's accuracy was confirmed on a series of training samples, she then hand-coded the cry samples as described above. It was these hand-coded cry samples that were used as the gold standard or ground truth for subsequent analyses of the accuracy of the automated system. Each frame required the careful labeling of 4 to 15 (or more if hyper-pitch) $F_0$ onsets; some 2915 frames were hand labeled. To cross-validate the hand-labeled ground truth, the same criteria were applied by an independent labeler used to hand label a little less than 10% of the frames (256). The ROC curve and an expansion of the "knee" part of the curve are shown in FIGS. 5A and 5B. It may be seen in this Figure that about 92% of the ground-truth data agree with those of the data independently labeled within a 2 Hz tolerance, and that there is 98% agreement within a 5 Hz tolerance. This provides a high degree of confidence in the ground truth data.

Fundamental Frequency

The results demonstrate accuracy of the $F_0$ estimation algorithm. The ground-truth labels were placed at sample indices of consistent peaks bracketing each pitch period during clearly voiced cries. There are clearly multiple pitch periods in each voiced frame. The sample indices were compared with the frame boundaries used by the analysis system to find all frames that were 100% covered by the pitch-period labels. The subset of frames for which hand-marked pitch-period labels were available are represented as $v_0$. The same set of cry recordings were processed by the analysis system, which output the set of estimated voiced frames v. The following analysis was carried out on $v \cap v0$, the set of all frames for which the automatic voicing labels, v, and the ground-truth voicing labels, $v_0$, agreed. The set $v \cap v_0$ contained a total of 2,915 voiced frames.

For each voiced frame in $v \cap v_0$, the magnitude of the error between the estimated pitch frequency, f, and the ground-truth pitch frequency, $F_0$, was computed. The pitch frequency estimate was considered to be correct if $|f-F_0| \leq T$, for some tolerance T in Hertz. One should note that the quantization tolerance in the cepstral domain varies from about 1 Hz at an $F_0$=200 Hz to about 5 Hz at $F_0$=1 kHz. FIG. 6 shows the percentage of frames with correct pitch-frequency estimates corresponding to each pitch-frequency tolerance, T. Several operating points are also shown in TABLE 4. As can be seen, the automated $F_0$ detection had an accuracy of about 90% at a tolerance of 10 Hz, and nearly 95% at a tolerance of 20 Hz. We did not see evidence for any systematic disagreement between the hand-coded and automated $F_0$ detection.

TABLE 4

Percentage of the 2,915 voiced frames with correct pitch-frequency estimates ($|f - f_0| \leq T$) for several error tolerances (T in Hz).

| Tolerance T (Hz) | % Correct Frames |
|---|---|
| 10 | 88.44 |
| 20 | 94.17 |
| 30 | 95.33 |
| 40 | 96.12 |
| 50 | 96.43 |

Figure 7:
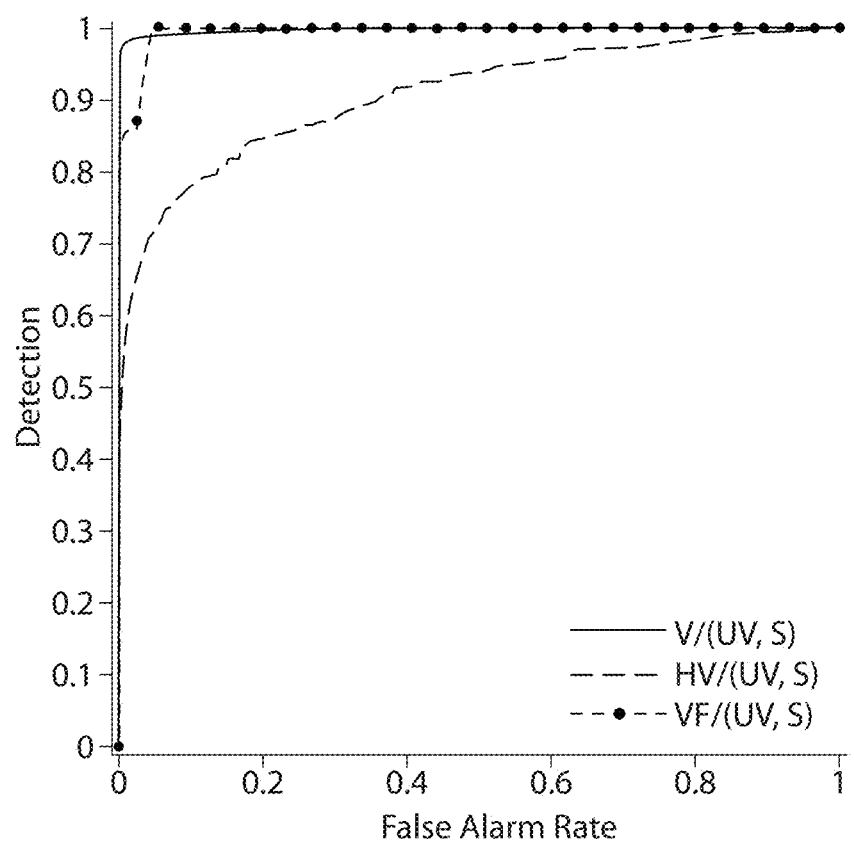
FIG. 7 shows ROC curves giving the voicing-detection performance of the system. Voiced (V), voiced-fricative (VF), and high-voiced (HV) frames were separately considered to be positives. In each case, both unvoiced (UV) and silence (S) frames were considered to be negatives. Area under the curve (Az) values were: V/(UV,S)=0.997; HV/(UV,S)=0.907; VF/(UV,S)=0.995.

Voicing:

A separate analysis was carried out to evaluate voicing-detection capabilities of the system. This analysis was formulated as a simple two-category classification problem, and FIG. 7 gives standard Receiver Operating Characteristic (ROC) curves showing the evaluation results. FIG. 7 includes silence (S) frames. The system is very effective in distinguishing voiced (V) frames from unvoiced (UV) and silence (S) frames. As expected, the system achieves much higher error rates when attempting to detect voiced frication (VF), which by definition are a mixture of voicing and turbulent signals. The HV frames were also more difficult to detect, although they occurred infrequently in this data set. Area under the curve (Az) values demonstrate accurate detection of voiced sound segments. Az values ranged from 0.907 to 0.997 for the analysis that included frames with silence, and 0.883 to 0.995 for frames that did not include silence.

The infant-cry analyzer described herein can be run in near-real-time on a normal PC platform, or could be run in real-time on many of today's embedded processors. It's overall design involved several years of collaborative effort between hospital-based and engineering-based faculty at Brown University, and resulted in a system that has utility for both basic and applied research on infant cry production. This system extends and builds upon recent approaches to quantifying acoustic features of infant cry (e.g., papers of Branco, et al., 2007; LaGasse et al., 2005; Lester, et al., 1991; Manfredi, et al., 2009; Varallyay, et al., 2004). This automated system is described in detail in order to provide the reader and potential users with a clear understanding of the approach that we used to develop this system. Quite uniquely, we conducted stringent tests of accuracy of this automated system as compared to hand-labeled cry spectrograms.

As detailed above, the apparatus analysis system has two levels of output. Phase I segments the sound into analysis frames with an advance of 12.5 ms. Each frame is summarized by the system for features that include timing, voicing, $F_0$, amplitude, and formant information. Phase II operates on the Phase I data, making decisions with regard to classifying portions of the sample as cry utterances or silence, which could be a portion of the recording prior to cry onset, or could represent time periods between cry utterances. This timing information allows researchers to utilize other measures such as latency to cry, which is of interest for researchers utilizing standard methods to elicit infant cries (LaGasse et al., 2005), and inter-utterance intervals, useful for classify different types of infant cries (e.g., pain vs. non-pain cries). In addition to this timing information, the Phase II output yields summary descriptors of cry utterances, including measures of $F_0$, amplitude of cry in various frequency bands, and estimates of formant location. This Phase II output also yields measures of the voiced proportion of each cry utterance. A unique aspect of this output is that it includes a confidence estimate for the voicing decision. This is based on an SNR analysis and allows the researcher both full information on how the voicing decision was made, as well as the ability to modify this decision, should the research question call for a more or less stringent definition of voicing.

An additional unique feature of the Phase II output is an automated approach to describing $F_0$ contours across a cry utterance. Some past research has made use of this variation in $F_0$ across utterances to describe "melodic" aspects of cries, but has accomplished this task by hand classification of $F_0$ contours from spectrograms (Mampe, Friederici, & Wermke, 2009; Wermke, Mende, Manfredi, & Bruscaglioni, 2002). The system described here utilizes a polynomial fit method to classify $F_0$ contours. Initially, the system classifies these contours into one of ten categories. This output may be used to identify cry utterances with more or less prototypical contours, to characterize the complexity of such $F_0$ variation, or to explore differences in $F_0$ contours related to development or population differences. The validity of an automated acoustic analysis is dependent on its performance accuracy. Therefore, we conducted a substantial experiment that indicates the accuracy of both the voicing and the fundamental frequency detectors. The features that were selected, i. e., $F_0$ and voicing, are the ones that have proven to be most discriminating of clinical populations in past literature.

Figure 6A:
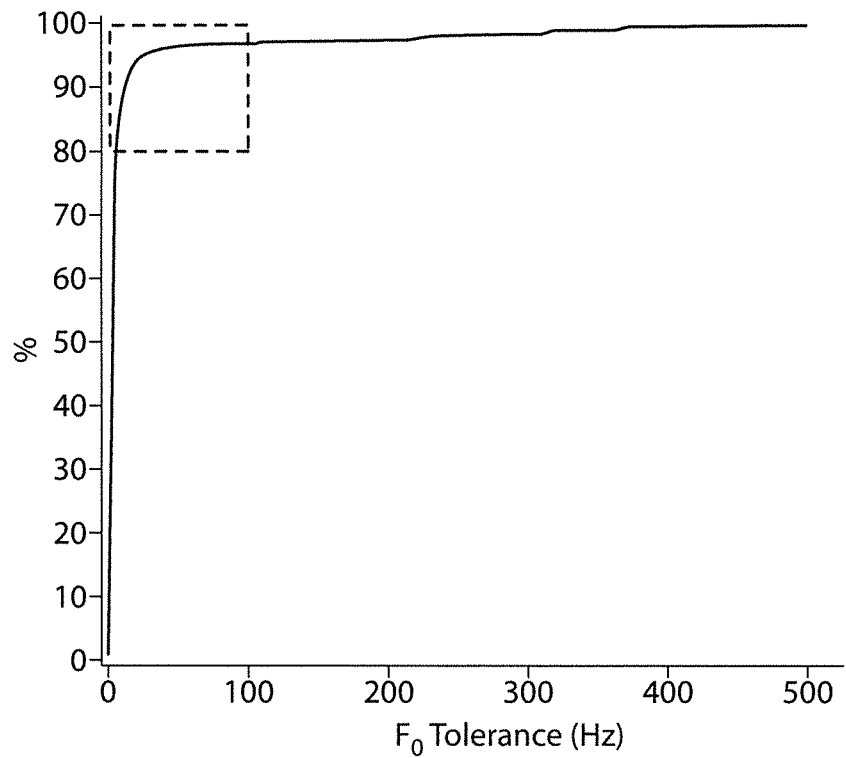
FIG. 6A shows the Percentage of the 2,915 voiced frames with correct pitch-frequency estimates ($|f-F_0| \le T$) for several error tolerances (T, in Hz)
Figure 6B:
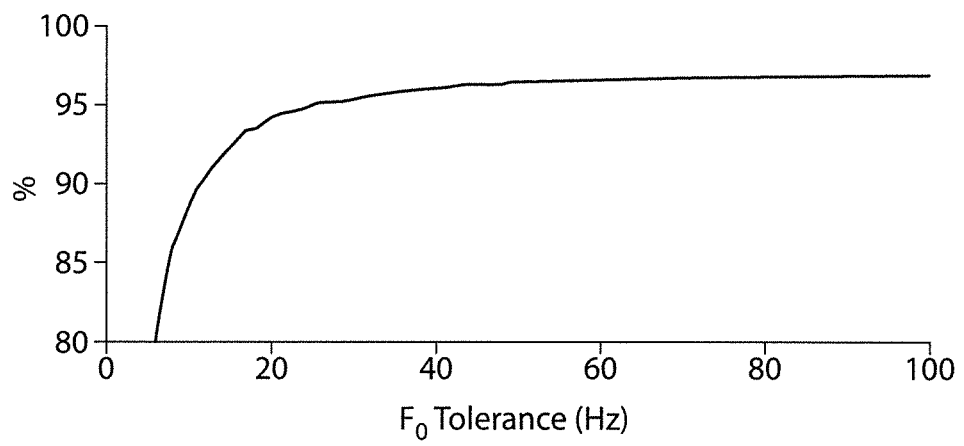
FIG. 6B is an expanded graph of the dotted area of FIG. 6A.

As depicted in FIGS. 6A and 6B, about 90% of the automatic estimates were within a $F_0$ tolerance of 10 Hz. The best the estimator does is 96.4% when the tolerance is opened up a bit to 50 Hz. Virtually all errors occur at the boundaries of voiced utterances. Equal-error rates for voiced (versus unvoiced or silence frame detection) is nearly 99%. Much more difficult to detect hyper-pitch frames are identified with an equal-error rate of about 80%. Past research utilizing automated analyses of infant cry has generally not reported this type of performance analysis. Further, other computer-assisted methods have utilized analyzers designed for adult speech. Validation of a system specifically designed to summarize the acoustic features of infant cry is therefore an advance in the field, and a unique strength of the methodology and apparatus reported here. Evaluation revealed high accuracy of the automatic detectors of $F_0$ and voicing decisions in comparison to gold standard hand coding from spectrogram displays.

The analysis system yields an excellent reduced data representation of the desired acoustic features of babies' cries, and may be used as a record to document cry characteristics, and a diagnostic tool for atypical characteristics. However, there are some areas of analysis that are a significant challenge for infant cry analysis. In particular, the accurate automatic detection of formants is quite difficult given the high pitch and wide harmonic structure of infant cry (Robb & Cacace, 1995). In adult speech, the shape of the vocal tract determines the resonant frequencies, which are described as formants. For our purposes, we applied a low-pass "lifter" to the data in order to assist in estimating the location and magnitude of formants in the infant cry. We have described this approach, but we acknowledge that the problem of both the measurement and interpretation of formants in infant cry remains to be fully resolved. An additional challenge is to reliably determine voicing in conditions that we refer to as voiced-fricative or high-voicing portions of a cry utterance. These issues are a reflection of some of the conceptual and methodological challenges to further development of the system, and to infant cry analysis more generally. On balance, the automated nature of this analysis system makes possible rapid analysis for large datasets and thus studies of substantial numbers of subjects, allowing for more powerful studies of differences in infant cry associated with various medical or developmental conditions or populations and more accurate detection of characterizing cry features. The system enables a researcher to summarize broad characteristics of cry utterances using the Phase II output, while also preserving detailed micro-analytic data in the Phase I output that would allow for precise characterization of within utterance variations in cry production.

Further embodiments of the invention are contemplated, including the detection of possible individual or group differences in cry production to help to screen for infants at risk for various developmental disorders, or it may find use in medical applications, such as identifying infants at risk for poor developmental outcomes. Thus, a validated cry analyzer will be useful for continued research on developmental outcomes in at risk infants, including investigations of neurobehavioral outcomes associated with prenatal environmental risk factors. Moreover, the complex nature of infant cry acoustics has the potential to yield feature patterns that can be used to identify infants at elevated risk for poor developmental outcomes or specific developmental disorders such as autism spectrum disorders. More basic research may also utilize this system in order to study normative aspects of infant cry production with larger samples than has been possible in the past. Instruments for recording and analysis, or for analysis of existing recordings, may include other processing steps and feature-identifying stages, and may include a user-friendly interface to enhance the accessibility of for a variety of researchers technical or support staff.

The invention now having been fully described, it is further exemplified by the following claims.

What is claimed is:

1. A method for diagnosing a developmental disorder in an infant by analyzing cry of the infant, the method comprising:

filtering a digital recording of an infant cry, by assigning to a digital signal of the recording: a fixed frame rate of a plurality of samples, a window function, and a frame advance, thereby obtaining an altered digital signal, and limiting a range of accepted frequency by applying a frequency window to a log-spectrum of the altered digital signal, wherein the frequency window is from about 200 Hz to about 2200 Hz, thereby obtaining a first filtered digital signal, wherein the first filtered digital signal is a frequency window output;

estimating a fundamental frequency and a cepstrum value of the infant cry by applying to the first filtered digital signal an inverse discrete Fourier transform to obtain the fundamental frequency and cepstrum estimate value of the first filtered digital signal, thereby obtaining a second filtered digital signal;

smoothing the second filtered digital signal by applying a programming smoother to the second filtered digital signal and maintaining continuity in the fundamental frequency estimates of the second filtered digital signal, eliminating outliers from the second filtered digital signal by applying a median filter, wherein the median filter is selected from a group of a median filters of five point and seven point median filters, to the second filtered digital signal and obtaining a median filter output, extracting a confidence measure from at least one of the first filtered digital signal values and the second filtered digital signal on a frame by frame basis, and applying to the median filter output a signal-to-noise ratio test, so as to obtain at least one parameter of acoustic analysis of the infant cry;

obtaining a data set having at least one parameter of acoustic analysis from a first group of normal infant subjects, and from a second group of infants having a developmental disorder or at risk for having a developmental disorder to correlate at least one parameter of acoustic analysis to an indicator of the disorder or risk; and diagnosing a presence of a developmental disorder in the infant by comparing at least one parameter of acoustic analysis to the data set.

2. The method according to claim 1, further estimating the fundamental frequency of the first filtered digital signal, if, greater than about 800 Hz, by applying an interpolated transform of 4096 points and a low pass filter.

3. The method according to claim 1, further comprising after applying the signal to noise ratio test, classifying a sound segment of the infant cry within the parameters as at least one of: an utterance, a short utterance, and a silence, wherein the sound segment comprises a group of frames having similar properties.

4. The method according to claim 3, further comprising characterizing a sound segment record by each of elements: classifier output, timing parameters, F0 parameters, hyper-pitch parameters, formant parameters, parameters from fitting a polynomial to the pitch contour, and parameters for amplitudes from several octave frequency bands.

5. The method according to claim 1, wherein the parameter of acoustic analysis comprises at least one of: frame number, time (ms), $F_0$, $F_0$ amplitude (dB), $F_0$ confidence [0-1], hyper-pitch (Hz) ([1-5] kHz range), hyper-pitch amplitude (dB), hyper-pitch confidence [0-1], peak pitch amplitude (dB), overall amplitude (dB), amplitude [0.5-10] kHz (dB), amplitude [0-0.5] kHz (dB), amplitude [0.5-1] kHz (dB), amplitude [1-2.5] kHz (dB), amplitude [2.5-5] kHz (dB), amplitude [5-10] kHz (dB), $F_1$ (Hz), amplitude of $F_1$ (dB), $F_2$ (Hz), amplitude of $F_2$ (dB), $F_3$ (Hz), and amplitude of $F_3$ (dB).

6. The method according to claim 1, further comprising prior to filtering the digital recording, converting the digital recording into a computer readable format by a computer program embedded in a non-transitory computer readable medium.

7. The method according to claim 3, wherein the utterance has a signal length equal to or greater than 0.5 s.

8. The method according to claim 1, wherein estimating the fundamental frequency of the infant cry further comprises validating, wherein the estimate has an accuracy of at least about 80%, about 85%, about 90%, about 95%, or at least about 99%.

9. The method according to claim 6, wherein the computer readable format is a .csv file of values of the parameters of acoustic analysis.

10. The method according to claim 1, wherein the developmental disorder is selected from the group of: Autism spectrum disorders selected from the group of: Autistic disorder, Asperger's disorder, child disintegrative disorder, Retts disorder, pervasive developmental disorder NOS, and Autism spectrum disorder; communication disorders selected from the group of: developmental language disorders, mixed-expressive receptive language disorder, language disorder, speech disorder, and social communication disorder; intellectual developmental disorders selected from the group of: intellectual developmental disorder and intellectual or global developmental delay not elsewhere classified; hearing impairment; cognitive impairment; language impairment; behavior disorders; and impairments or deficits related to "high risk" conditions exemplified by prenatal substance exposure, prematurity, low birth weight, intrauterine growth retardation, medical illness or brain injury, maternal history of mental illness, treatment, adverse pregnancy conditions exemplified by poor nutrition, poor prenatal care, physical assault, and genetic conditions that increase risk for cognitive, language, or behavioral impairments.

11. The method according to claim 1, further comprising after obtaining the digital recording of the infant cry, classifying a portion of infants that have the disorder from among a plurality of the infants.

12. The method according to claim 11, further comprising after obtaining the digital recording of the infant cry classifying retrospectively the portion of infants that have the disorder.

13. The method according to claim 1 further comprising, applying a stimulus to an infant, wherein the stimulus stimulates the infant cry in reaction.

14. The method according to claim 13, wherein the infant cry is stimulated by applying a pain stimulus.

15. The method according to claim 1, wherein the infant cry is spontaneous.

16. The method according to claim 1, wherein the method distinguishes a pain induced cry and a spontaneous cry.

17. The method according to claim 1, further comprising after diagnosing the presence of the developmental disorder, administering early intervention to the infant.

18. An apparatus for analyzing an infant cry, the apparatus comprising,
a recording device adapted and configured to record the infant cry, thereby obtaining a digital signal of a recorded infant cry,
a computer program embedded in a non-transitory computer readable medium, the computer readable medium comprising instructions to perform the method of claim 1, and
a computer, wherein the recording device and the non-transitory computer readable medium are compatible with the computer and are linkable to the computer.

19. The apparatus according to claim 18, wherein the parameter of acoustic analysis comprises at least one of: frame number, time (ms), $F_0$, $F_0$ amplitude (dB), $F_0$ confidence [0-1], hyper-pitch (Hz) ([1-5] kHz range), hyper-pitch amplitude (dB), hyper-pitch confidence [0-1], peak pitch amplitude (dB), overall amplitude (dB), amplitude [0.5-10] kHz (dB), amplitude [0-0.5] kHz (dB), amplitude [0.5-1] kHz (dB), amplitude [1-2.5] kHz (dB), amplitude [2.5-5] kHz (dB), amplitude [5-10] kHz (dB), $F_1$ (Hz), amplitude of $F_1$ (dB), F2 (Hz), amplitude of $F_2$ (dB), $F_3$ (Hz), and amplitude of $F_3$ (dB).

20. The apparatus according to claim 18, further comprising, a stimulating component, wherein the stimulating component provides a stimulus to an infant so as to initiate the infant cry in reaction.

21. Apparatus for infant cry analysis comprising means for:
receiving a digital sound recording or digitizing an analog sound recording of an infant cry, wherein the sound recording is a consumer-device-formatted sound recording or other standard format,
limiting the recording to a frequency range of about 200-2200 Hz representing a frequency band of interest and segmenting the recording into cry segments by type, wherein the segment types include intervals of silence, short cries and long cries, performing computerized acoustic analysis on each segment to identify acoustic parameters of the recording according to method described in claim 1, wherein the acoustic parameters include one or more of frame number, time (ins), $F_0$, $F_0$ amplitude (dB), $F_0$ confidence [0-1], hyper-pitch (Hz) ([1-5] kHz range), hyper-pitch amplitude (dB), hyper-pitch confidence [0-1], peak pitch amplitude (dB), overall amplitude (dB), amplitude [0.5-10] kHz (dB), amplitude [0-0.5] kHz (dB), amplitude [0.5-1] kHz (dB), amplitude [1-2.5] kHz (dB), amplitude [2.5-5] kHz (dB), amplitude [5-10] kHz (dB), $F_1$ (Hz), amplitude of $F_1$ (dB), $F_2$ (Hz), amplitude of $F_2$ (dB), $F_3$ (Hz), and amplitude of $F_3$ (dB), and providing the detected parameters as a spreadsheet file for use as a validated medical or diagnostic record.

22. Apparatus according to claim 21, further comprising diagnostic software for highlighting diagnostic indicia among the reported parameters, wherein the diagnostic indicia reflect likelihood that the infant cry indicates a developmental or neurological condition such as ASD, or a medical condition such as an airway or tissue anomaly.

23. Apparatus according to claim 21, further comprising a cry stimulus device adapted and configured to providing a controlled cry-provoking stimulus to an infant synchronized with recording of the infant's cry, and further comprising a video recorder for validating cry data.

* * * * *

UNITED STATES PATENT AND TRADEMARK OFFICE
CERTIFICATE OF CORRECTION

PATENT NO. : 10,278,637 B2  
APPLICATION NO. : 14/633224  
DATED : May 7, 2019  
INVENTOR(S) : Sheinkopf et al.

Page 1 of 1

It is certified that error appears in the above-identified patent and that said Letters Patent is hereby corrected as shown below:

In the Claims

Claim 21, Column 23, Line 7:
Delete: "(ins)"
Insert: --(ms)--

Signed and Sealed this
Eighteenth Day of June, 2019

Andrei Iancu
*Director of the United States Patent and Trademark Office*